US007414115B2

(12) United States Patent
Livak et al.

(10) Patent No.: US 7,414,115 B2
(45) Date of Patent: Aug. 19, 2008

(54) LENGTH DETERMINATION OF NUCLEIC ACID REPEAT SEQUENCES BY DISCONTINUOUS PRIMER EXTENSION

(75) Inventors: Kenneth J. Livak, San Jose, CA (US); Adam L. Lowe, San Francisco, CA (US); Andrew J. Blasband, Redwood, CA (US)

(73) Assignee: Applied Biosystems Inc., Foster City, CA (US)

(*) Notice: Subject to any disclaimer, the term of this patent is extended or adjusted under 35 U.S.C. 154(b) by 0 days.

(21) Appl. No.: 11/731,192

(22) Filed: Mar. 30, 2007

(65) Prior Publication Data

US 2007/0178519 A1 Aug. 2, 2007

Related U.S. Application Data

(60) Division of application No. 10/892,403, filed on Jul. 14, 2004, which is a continuation of application No. 10/038,520, filed on Oct. 22, 2001, now Pat. No. 6,773,887, and a continuation of application No. 09/205,114, filed on Dec. 3, 1998, now Pat. No. 6,309,829, and a continuation-in-part of application No. 08/863,437, filed on May 27, 1997, now Pat. No. 5,945,284.

(51) Int. Cl.
*C07H 19/00* (2006.01)
*C07H 21/02* (2006.01)
*C07H 21/04* (2006.01)
*C12Q 1/68* (2006.01)
*C12P 19/34* (2006.01)

(52) U.S. Cl. .................. 536/22.1; 536/23.1; 536/24.33; 435/6; 435/91.2

(58) Field of Classification Search .................. 435/6, 435/91.2; 536/23.1, 22.1, 24.33
See application file for complete search history.

(56) References Cited

U.S. PATENT DOCUMENTS

| 5,075,217 A | 12/1991 | Weber |
| 5,302,509 A | 4/1994 | Cheeseman |
| 5,367,066 A | 11/1994 | Urdea et al. |
| 5,374,527 A | 12/1994 | Grossman |
| 5,436,130 A | 7/1995 | Mathies et al. |
| 5,512,439 A | 4/1996 | Hornes et al. |
| 5,518,900 A | 5/1996 | Nikiforov |
| 5,541,067 A | 7/1996 | Perlin |
| 5,547,839 A * | 8/1996 | Dower et al. .................. 435/6 |
| 5,580,728 A | 12/1996 | Perlin |
| 5,610,287 A | 3/1997 | Nikiforov |
| 5,650,277 A | 7/1997 | Navot |
| 5,695,933 A | 12/1997 | Schalling et al. |
| 5,753,439 A | 5/1998 | Smith et al. |
| 5,767,259 A | 6/1998 | Albagi et al. |
| 5,945,284 A * | 8/1999 | Livak et al. .................. 435/6 |
| 5,981,176 A | 11/1999 | Wallace |
| 6,309,829 B1 * | 10/2001 | Livak et al. .................. 435/6 |

FOREIGN PATENT DOCUMENTS

| DE | 41411178 A1 | 6/1993 |
| FR | 2718753 A1 | 10/1995 |
| WO | WO 91/13075 A2 | 9/1991 |
| WO | WO 92/15712 A1 | 9/1992 |
| WO | WO 93/17126 A1 | 9/1993 |
| WO | WO 94/21820 A1 | 9/1994 |
| WO | WO 96/31622 A1 | 10/1996 |
| WO | WO 96/36737 A1 | 11/1996 |
| WO | WO 96/41011 A1 | 12/1996 |
| WO | WO 97/31256 A2 | 8/1997 |
| WO | WO 98/54362 A1 | 12/1998 |

OTHER PUBLICATIONS

Canard, et al., "Catalytic Editing Properties of DNA Polymerase,"Proc. Natl. Acad. Sci. USA 92: 10859-10863, Nov. 1995.
Clemens, et al., "Carrier Detection and Prenatal Diagnosis in Duchenne and Becker Muscular Dystrophy Families, Using Dinucleotide Repeat Polymorphisms."Am. J. Human Genetic. 49: 951-960 (1991).
Jeffreys, et al., "Repeat Unit Sequence Variation in Minsatellites: A novel Source of DNA Polymorphism for Studying Variation and Mutation by Single Molecule Anaylsis" Cell 60: 473-485 (1990).
Litt and Luty, "A Hypervariable Microsatellite Revealed by In Vitro Amplification of A Dinucleotide Repeat within the Cardiac Muscle Actin Gene," Am. J. Human Genet. 44:397-401 (1997).
Mansfield, et al., "Rapid Sizing of Polymorphic Microsatellite Markers by Capillary Array Electrophoresis,"J. Chromatography 781 (1+2) :295-305 (1997).
Matthews and Kricka, "Analytical Strategies for the Use of DNA Probes," Analytical Biochem. 169:1-25 (1988).
Metzker, et al., "Termination of DNA Synthesis by Novel 3'-Modified-Deoxyribonucleoside 5'-Triphosphate,". Nuc. Acids Res. 22(20):4259-4267 (1994).
Neilan, et al., "Microsatellite Genome Screeing: Rapid Non-Denaturing, Non-Isotopic Dinucleotide Repeat Analysis,"BioTechniques 17(4):708-712 (1994).
Perlin, et al., "Toward Fully Automated Genotyping : Allele Assignment, Pedigree Construction, Phase Determination, and Recombination Detection in Duchenne Muscular Dystrophy,"Am. J. Him. Genet. 55:777-787 (1984).
Search Report from related PCT Application No. PCT/US98/09657.

(Continued)

Primary Examiner—Suryaprabha Chunduru
(74) Attorney, Agent, or Firm—William D. Schmidt; Kalow & Springut LLP

(57) ABSTRACT

Disclosed is a kit useful for determining the number of repeat units in a repeat region of a target nucleic acid comprising: a plurality of different-sequence primers, each containing (i) a target binding segment and (ii) a tag segment having a nucleotide sequence that uniquely identifies the target binding segment, a first primer extension reagent; and a second primer extension reagent, wherein at least one of the first or second primer extension reagents includes an extendible nucleotide having a photodestructible label attached thereto.

9 Claims, 7 Drawing Sheets

OTHER PUBLICATIONS

The Dynal Catalog/Technical Handbook, pp. 116-119 (1995).

The Stratagene Catalog, p. 39 (1988).

Weber and May, "Abundant Class of Human DNA Polymorphisms which can be Typed Using the Polymerase Chain Reaction," Am. J. Hum. Genet. 44:388-396 (1989).

* cited by examiner

SEQUENCE LISTING

```
<160> NUMBER OF SEQ ID NOS: 4

<210> SEQ ID NO 1
<211> LENGTH: 34
<212> TYPE: DNA
<213> ORGANISM: Artificial Sequence
<220> FEATURE:
<223> OTHER INFORMATION: oligo 2260-2G

<400> SEQUENCE: 1
gtcaggacac aaagtgattt gatgtagatt ttga                                   34

<210> SEQ ID NO 2
<211> LENGTH: 32
<212> TYPE: DNA
<213> ORGANISM: Artificial Sequence
<220> FEATURE:
<223> OTHER INFORMATION: oligo 1411-1G

<400> SEQUENCE: 2
gtcaggactg ataaagtgta aaagtgtatg at                                     32

<210> SEQ ID NO 3
<211> LENGTH: 34
<212> TYPE: DNA
<213> ORGANISM: Artificial Sequence
<220> FEATURE:
<223> OTHER INFORMATION: oligo 3149-2T

<400> SEQUENCE: 3
gtcattacac tgtatgataa aggattttga ttga                                   34

<210> SEQ ID NO 4
<211> LENGTH: 38
<212> TYPE: DNA
```

```
-continued

<213> ORGANISM: Artificial Sequence
<220> FEATURE:
<223> OTHER INFORMATION: oligo 4223-4T

<400> SEQUENCE: 4
gtcattacac acacgtattg atttgattga ttgagatt                          38
```

LENGTH DETERMINATION OF NUCLEIC ACID REPEAT SEQUENCES BY DISCONTINUOUS PRIMER EXTENSION

CROSS-REFERENCE TO RELATED APPLICATIONS

This application is a divisional of U.S. Ser. No. 10/892,403, filed Jul. 14, 2004, which is a continuation of U.S. Ser. No. 10/038,520, filed on Oct. 22, 2001, which is a continuation of U.S. Ser. No. 09/205,114, filed on Dec. 3, 1998, which issued as U.S. Pat. No. 6,309,829 on Oct. 30, 2001, and which is a continuation-in-part of U.S. Ser. No. 08/863,437, filed on May 27, 1997, which issued as U.S. Pat. No. 5,945,284 on Aug. 31, 1999. The present application claims the benefit of the filing dates of the aforementioned applications and patents and incorporates their disclosures herein by reference.

FIELD OF THE INVENTION

This invention relates to methods and kits useful for determining the length of nucleic acid repeat sequences. More specifically, this invention relates to methods and kits useful for determining the length of nucleic acid repeat sequences by employing a discontinuous primer extension reaction.

REFERENCES

Ausubel et al. eds., *Current Protocols in Molecular Biology Volume* 1, Chapter 2, Section I, John Wiley & Sons, New York (1993).
Barany et al., International Patent Application PCT/US91/06103.
Beattie et al., *Clinical Chemistry*, 39:719-722 (1993).
Beaucage and Iyer, *Tetrahedron*, 48: 2223-2311 (1992).
Boom et al., U.S. Pat. No. 5,234,809.
Brenner, PCT Publications No. WO 96/12014 and WO 96/41011.
Breslauer et al., *Proc. Natl. Acad. Sci.* 83:3746-3750 (1986).
Bronstein, et al., *J. Biolumin. Chemilumin.*, 4: 99-111 (1990).
Cantor et al, U.S. Pat. No. 5,482,836.
Caskey and Edwards, U.S. Pat. No. 5,364,759.
Chidgeavadze et al., *Nucleic Acids Res.* 12: 1671-1686 (1984); Chidgeavadze et al., *FEB. Lett.*, 183: 275-278 (1985); and Chidgeavadze et al., *Biochim. Biophys. Acta* 868:145 (1986).
Damha et al., *Nucleic Acids Research*, 18:3813-3821 (1990).
Drmanac, R., et al., *Electrophoresis* 13:566 (1992).
Drmanac, R., et al., *Science* 260:1649 (1993).
Dieffenbach et al., in *PCR Primer: A Laboratory Manual*, Diffenbach and Dveksler, eds., p 133-142, CSHL Press, New York (1995).
Eckstein, F., *Oligonucleotides and Analogs: A Practical Approach*, Chapters 8 and 9, IRL Press, Oxford, GB (1991).
Fodor, S. P. A., et al., *Science* 251:767 (1991).
Fodor, S. P. A., et al., U.S. Pat. No. 5,445,934 (1995).
Guo et al., Nucleic Acids Research, 22(24): 5456-5465 (1994).
Jabs et al., *Proc. Natl. Acad Sci.*, 86: 202 (1989).
Jeffreys et al., *Cell*, 60: 473 (1990).
Ji et al., *Anal. Chem.* 65:1323-1328 (1993).
Johnston, R. F., et al., *Electrophoresis* 11:355 (1990).
Khan et al., U.S. patent application Ser. No. 08/696,808.
Khrapko, K. R., et al., *DNA Sequencing* 1:375 (1991).
Knudsen, H., et al., *Nucleic Acids Res.* 24:494-500 (1996).
Kornberg and Baker, *DNA Replication* 2nd Eddition, W. H. Freeman, New York (1991).
Krayevski, A., et al., *Biochim. Biophys. Acta* 783:216 (1984).
Kricka, in *Nonisotopic DNA Probe Techniques*, Kricka ed., Chapter 1, Academic Press (1992).
Maskos and Southern, *Nucleic Acids Research*, 20:1679-1684 (1992).
Mathies, R. A., et al., U.S. Pat. No. 5,091,652 (1992).
Metzker et al., *Nucleic Acids Research*, 22(20): 4259 (1994).
Mikhailopulo et al., *FEB Lett.* 250:139 (1989)
Miller et al., *Nucleic Acids Research*, 16(3): 9-10 (1988).
Montpetit et al., *J. Virol. Methods*, 36: 119-128 (1992).
Mullis, U.S. Pat. Nos. 4,683,195; 4,683,195; and 4,683,202.
Osborne, *CABIOS*, 8: 83 (1991).
Pease et al., *Proc. Natl. Acad. Sci.*, 91:5022-5026 (1994).
*Pierce Catalog and Handbook*, Pierce Chemical Co. (1994).
Ploem, J. S., in *Fluorescent and Luminescent Probes for Biological Activity*, Mason, T. W., Ed., Academic Press, London, pp. 1-11 (1993).
Pon et al., *Biotechniques*, 6:768-775 (1988).
Ruby et al., *Methods in Enzymology*, 181: 97 (1990).
Rychlik et al., *Nucleic Acids Res.* 17:8543-8551 (1989) and 18:6409-6412 (1990).
Scheit, *Nucleotide Analogs*, John Wiley Pub., New York (1980).
Schena, M., et al., *Science* 270:467 (1995).
Shoemaker et al., European Pub. No. EP 799,897 A1 (1997).
Smeets et al., *Hum. Genet*, 83: 245 (1989).
Southern et al., *Genomics*, 13:1008-1017 (1992).
Stryer, L., *Biochemistry*, $2^{nd}$ Edition, W. H. Freeman and Co., San Francisco, Calif. (1981) and subsequent editions.
Walsh et al., *Biotechniques* 10(4): 506-513 (1991).
Webb, U.S. Pat. No. 4,659,774.
Webber and May, *Am. J. Hum. Genet.*, 44: 388 (1989).
Wetmur, *Crit. Rev. Biochem. Mol. Biol.* 26:227-259 (1991).
Williamson et al., *Cytogenet. Cell. Genet.*, 55: 457 (1990).
Yershov, G., et al., *Proc. Natl. Acad. Sci.* 93:4913 (1996).

BACKGROUND

Methods for the analysis of genetic polymorphism have found wide utility in basic research, clinical diagnostics, forensics, and other areas. One particularly useful method of detecting genetic polymorphism is based on variations in the length of repeat sequences, such methods being variously referred to as short tandem repeat analysis (STR), variable number of tandem repeat analysis (VNTR), minisatellite analysis, and microsatellite analysis.

Detection of length polymorphisms in nucleic acid repeat sequences has up to now relied on gel electrophoresis for the determination of the length of the repeat sequence. However, gel electrophoresis has several important drawbacks in the context of repeat sequence length polymorphism analysis. First, molecular length measurements based on electrophoretic mobility are inherently, imprecise due to a complicated relationship between molecular size and electrophoretic mobility. Second, the degree to which the electrophoretic process can be multiplexed is limited by the number of electrophoresis lanes and by the size of different

SUMMARY

The method of the present invention comprises a discontinuous primer extension reaction wherein a primer is extended in discrete increments such that in each increment of primer extension the primer is extended by an amount corresponding to a single repeat unit. Following each increment of discrete primer extension, a detection step is performed in which a modulation in a signal is detected when the primer has been extended by an amount equal to the total length of a repeat region. Thus, by counting the number of increments of discrete primer extension required to cause a modulation in the signal, the number of repeat units making up the repeat region is determined.

It is an object of the present invention to provide a precise and reproducible method for determining the number of repeat units making up a repeat region of a nucleic acid repeat sequence.

It is another object of the present invention to provide a method for determining the number of repeat units making up a repeat region of a nucleic acid repeat sequence which can perform a large number of measurements in parallel.

It is yet an additional object of the present invention to provide a method for determining the number of repeat units malking up a repeat region of a nucleic acid repeat sequence which does not require an electrophoretic separation.

It is an object of the present invention to provide kits and reagents useful for practicing a method for determining the number of repeat units making up a repeat region of a nucleic acid repeat sequence having the above described characteristics.

In a first aspect, the foregoing and other objects of the invention are achieved by a method for determining the number of repeat units in a repeat region of a target nucleic acid comprising annealing a primer-complementary portion of a target nucleic acid to a primer thereby forming a target-primer hybrid; performing a first primer extension reaction using a first primer extension reagent; separating the target-primer hybrid and unreacted first primer extension reagent; performing a second primer extension reaction using a second primer extension reagent, wherein at least one of the first or second primer extension reagents includes an extendible nucleotide having a label attached thereto; separating the target-primer hybrid from unreacted second primer extension reagent; measuring a signal produced by the label; treating the label so as to render the label undetectable; and repeating the above steps until the signal is substantially less than a signal detected in a previous cycle.

In one preferred embodiment of the first aspect of the invention, the step of performing a second primer extension reaction further includes reacting the target-primer hybrid with a primer termination reagent.

In yet another preferred embodiment of the first aspect of the invention, the label is a fluorescent or chemiluminescent molecule.

In another preferred embodiment of the first aspect of the invention, the label is attached to the extendible nucleotide through a cleavable linker.

In an additional preferred embodiment of the first aspect of the invention, the target nucleic acid is amplified prior to analysis. Preferably such amplification is achieved using a PCR.

In an another preferred embodiment of the first aspect of the invention, the step of treating the label so as to render the label undetectable includes either cleaving the label from the labeled extendible nucleotide or destroying a signal producing property of the label.

In another preferred embodiment of the first aspect of the invention, the target-primer hybrid is attached to a solid support. Preferably, one of the primer or the target nucleic acid is attached to the solid support.

In a novel, preferred embodiment employing a solid support, the invention includes a method for determining the number of repeat units in a repeat region of a target nucleic acid comprising the steps of:

(A) contacting a plurality of different-sequence primers with a polynucleotide sample under conditions effective for the primers to anneal to primer-complementary regions in one or more target polynucleotides, to form one or more target-primer hybrid(s), wherein either (1) each different-sequence primer contains (i) a target binding segment and (ii) a, tag segment having a nucleotide sequence that uniquely identifies the target binding seament, or (2) one or more polynucleotides in the sample are tagged polynucleotides that contain a tag segment having a nucleotide sequence that uniquely identifies the attached polynucleotide, (B) performing a first primer extension reaction on the hybrid(s) using a first primer extension reagent;

(C) separating the target-primer hybrid(s) and unreacted first primer extension reagent;

(D) performing a second primer extension reaction on the hybrid(s) using a second primer extension reagent, wherein at least one of the first or second primer extension reagents includes an extendible nucleotide having a label attached thereto;

(E) separating the target-primer hybrid(s) from unreacted second primer extension reagent;

(F) measuring a signal produced by the label;

(G) treating the label so as to render the label undetectable; and (H) repeating a cycle of steps (A) through (G) until the signal detected in the target-primer hybrid(s) is substantially less than a signal detected in a previous cycle, wherein (I) prior to step (F), at least an aliquot of either (1) the different-sequence primers or (2) the tagged sample polynucleotides are contacted with an addressable array of immobilized, different tag complements, and each different tag complement contains a sequence that is complementary to one of the tag segments, under conditions effective to hybridize the tag segments to corresponding tag complements on the support.

In one embodiment, the contacting in step (I) is performed prior to step (A). In another embodiment, the contacting in step (I) is performed after step (A), and/or before any one of steps (B), (C), (D), (E), and (F). In yet another embodiment, steps (A) through (H) are performed on at least two replicate arrays, and one of the replicate arrays is subjected to at least one more cycle of steps (A) through (G) than is a second replicate array.

In a second aspect, the foregoing and other objects of the invention are achieved by a method for determining the number of repeat units in a repeat region of a target nucleic acid comprising annealing a primer-complementary portion of a target nucleic acid to a primer thereby forming a target-primer hybrid; performing a first primer extension reaction using a first primer-extension reagent; separating the target-primer hybrid from unreacted first primer extension reagent; performing a second primer extension reaction using a second primer extension reagent and with a primer termination reagent, the primer termination reagent including a nucleotide terminator having a label attached thereto; separating the target-primer hybrid from unreacted second primer extension reagent and unreacted primer termination reagent; measuring a signal produced by the label; and repeating the above steps until a signal is detected indicating incorporation of the labeled nucleotide terminator into the primer extension product.

In yet another preferred embodiment of the second aspect of the invention, the label is selected from the group consisting of fluorescent and chemiluminescent molecules.

In an additional preferred embodiment of the second aspect of the invention, the target nucleic acid is amplified prior to analysis. Preferably such amplification is achieved using a PCR.

In a preferred embodiment of the second aspect of the invention, the target-primer hybrid is attached to a solid support. Preferably, one of the primer or the target nucleic acid is attached to the solid support.

In a novel, preferred embodiment, the invention includes a method for determining the number of repeat units in a repeat region of a target nucleic acid comprising the steps of:

(A) contacting a plurality of different-sequence primers with a polynucleotide sample under conditions effective for the primers to anneal to primer-complementary regions in one or more target polynucleotides, to form one or more target-primer hybrid(s), wherein either (1) each different-sequence primer contains (i) a target binding segment and (ii) a tag segment having a nucleotide sequence that uniquely identifies the target binding segment, or (2) one or more polynucleotides in the sample are tagged polynucleotides that contain a tag segment having a nucleotide sequence that uniquely identifies the attached polynucleotide, (B) performing a first primer extension reaction on the hybrid(s) using a first primer-extension reagent;

(C) separating the target-primer hybrid(s) from unreacted first primer extension reagent;

(D) performing a second primer extension reaction on the hybrid(s) using a second primer extension reagent and with a primer termination reagent, the primer termination reagent including a nucleotide terminator having a label attached thereto;

(E) separating the target-primer hybrid(s) from unreacted second primer extension reagent and unreacted primer termination reagent;

(F) measuring a signal produced by the label; and (G) repeating a cycle of steps (A) through (F) until a signal is detected indicating incorporation of the nucleotide terminator, wherein (H) prior to step (F), at least an aliquot of either (1) the different-sequence primers or (2) the tagged sample polynucleotides, are contacted with an addressable array of immobilized, different tag complements, and each different tag complement contains a sequence that is complementary to one of the tag segments, under conditions effective to hybridize the tag segments to corresponding tag complements on the support.

In one embodiment, the contacting in step (H) is performed prior to step (A). In another embodiment, the contacting in step (H) is performed after step (A), and/or before any one of steps (B), (C), (D), (E), and (F). In yet another embodiment, steps (A) through (G) are performed on at least two replicate arrays, and one of the replicate arrays is subjected to at least one more cycle of steps (A) through (F) than is a second replicate array.

In a third aspect, the foregoing and other objects of the invention are achieved, by a kit useful for determining the number of repeat units in a repeat region of a target nucleic acid comprising a primer having a sequence complementary to a primer-complementary portion of a target nucleic acid; a first primer extension reagent; and a second primer extension reagent, wherein at least one of the first or second primer extension reagents includes an extendible nucleotide having a label attached thereto.

In a preferred embodiment of the third aspect of the invention, the primer is attached to a solid support.

In an additional preferred embodiment of the second aspect of the invention, the label is selected from the group consisting of fluorescent and chemiluminescent molecules.

In another preferred embodiment of the second aspect of the invention, the label is attached to the extendible nucleotide through a cleavable linker.

These and other objects, features, and advantages of the present invention will become better understood with reference to the following description, drawings, and appended claims.

DETAILED DESCRIPTION OF THE PREFERRED EMMODIMENTS

Figure 1:
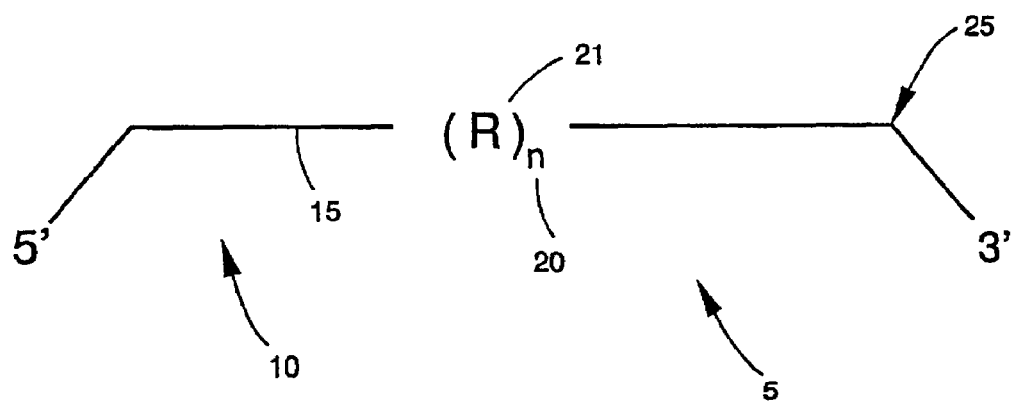
FIG. 1 shows a schematic depiction of a target nucleic acid.

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

I. Definitions

Unless stated otherwise, the following terms and phrases as used herein are intended to have the following meanings:

"Nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms (Stryer).

The term "nucleotide" as used herein refers to a phosphate ester of a nucleoside, e.g., a triphosphate ester, wherein the most common site of esterification is the hydroxyl group attached at the C-5 position of the pentose. Many times in the present disclosure the term nucleoside will be intended to include both nucleosides and nucleotides. The terms nucleotide and nucleoside as used herein are intended to include synthetic analogs having modified nucleoside base moieties, modified sugar moieties, and/or modified phosphate ester moieties, e.g., as described elsewhere (Scheit; Eckstein).

"Polynucleotide" or "oligonucleotide" refer to linear polymers of nucleotide monomers, including single, double and triple stranded deoxyribonucleotides, ribonucleotides, α-anomeric forms thereof, and the like. Usually the nucleoside monomers are linked by phosphodiester linkages, where as used herein, the term "phosphodiester linkage" refers to phosphodiester bonds or bonds including phosphate analogs thereof wherein the phosphorous atom is in the +5 oxidation state and one or more of the oxygen atoms is replaced with a non-oxygen moiety. Exemplary phosphate analogs include phosphorothioate, phosphorodithioate, phosphoroselenoate, phosphorodiselenoate, phosphoroanilothioate, phosphoranilidate, phosphoramidate, boronophosphates, and the like, including associated counterions, e.g., $H^+$, $NH_4^+$, $Na^+$, and the like if such counterions are present. Alternatively, polynucleotides may comprise polymers of non-nucleotidic monomers, linked through phosphodiester linkages or other linkages, which are capable of forming sequence-specific hybrids with a target nucleic acid, e.g., peptide nucleic acid polymers (PNAs, e.g., see Knudsen, 1996). Polynucleotides typically range in size from a few monomeric units, e.g. 8-40, to several thousands of monomeric units. Whenever a polynucleotide is represented by a sequence of letters, such as "ATGCCTG," it will be understood that the nucleotides are in 5'->3' order from left to right and that "A" denotes deoxyadenosine, "C" denotes deoxycytidine, "G" denotes deoxyguanosine, and "T" denotes thymidine, unless otherwise noted.

"Extendible nucleotide" means any nucleotide that when incorporated into a primer extension product during a primer extension reaction allows for the further extension of such primer extension product. Exemplary extendible nucleotides include 2'-deoxynucleotide triphosphates, e.g., 2'-deoxyuridine-5'-triphosphate, 2'-deoxyguanosine-5'-triphosphate, 2'-deoxy-7-deazadeoxyguanosine-5'-triphosphate, 2'-deoxyadenosine-5'-triphosphate, 2'-deoxythymidine-5'-triphosphate, and 2'-deoxycytidine-5'-triphosphate. Optionally, one or more of the extendible nucleotides includes a label.

"Nucleotide terminator" means any nucleotide that when incorporated into a primer extension product prevents the further extension of such primer extension product. One requirement of a nucleotide terminator is that when the nucleotide terminator includes a ribofuranose sugar portion, the 3'-position must not have a hydroxy group capable of being subsequently used by a polymerase to incorporate additional nucleotides. Alternatively, a ribofuranose analog could be used, such as arabinose. Exemplary nucleotide terminators include 2',3'-dideoxy-β-D-ribofuranosyl, β-D-arabinofuranosyl, 3'-deoxy-β-D-arabinofuranosyl, 3'-amino-2',3'-dideoxy-β-D-ribofuranosyl, and 2',3'-dideoxy-3'-fluoro-β-D-ribofuranosyl (Chidgeavadze, 1984, 1985). Nucleotide terminators also include reversible nucleotide terminators (Metzker), and 3'-deoxy substituents such as hydrogen, 3'-fluoro, 3'-amino, and 3'-azido, for example (Mikhailopulo et al., 1989; Krayevski et al., 1984; Chidgeavadze, 1986).

"Polymerase" means an enzyme or other catalyst capable of catalyzing a reaction leading to a target-sequence dependent incorporation of a nucleotide onto a 3'-end of a primer or primer extension product when such primer or primer extension product is annealed to a target nucleic acid. Exemplary polymerases include but are not limited to Pfr DNA polymerase, E. Coli Polymerase I, T-7 polymerase, reverse transcriptase, Taq DNA polymerase, and the like (Kornberg and Baker).

"Label" means any moiety that, when attached to a nucleotide or polynucleotide of the invention, render such nucleotide or polynucleotide detectable using known detection means. Labels may be direct labels which themselves are detectable or indirect labels which are detectable in combination with other agents. Exemplary direct labels include but are not limited to fluorophores, chromophores, radioisotopes, spin-labels, chemiluminescent labels, and the like. Exemplary indirect labels include enzymes which catalyze a signal-producing event, and ligands such as an antigen or biotin which can bind specifically with high affinity to a detectable anti-ligand, such as a labeled antibody or avidin.

"Primer extension reaction" means a reaction between a target-primer hybrid and a nucleotide which results in the addition of the nucleotide to an end of the primer, usually the 3'-end, such that the added nucleotide is complementary to the corresponding nucleotide of the target nucleic acid.

"Primer-extension reagent" means a reagent including components necessary to effect a primer extension reaction. Primer extension reagents typically include (i) a polymerase enzyme; (ii) a buffer; and (iii) one or more extendible nucleotides.

"Specific binding pair" refers to a pair of molecules that specifically bind to one another to form a binding complex. Examples of specific binding pairs include, but are not limited to antibody-antigen (or hapten) pairs, ligand-receptor pairs, enzyme-substrate pairs, biotin-avidin pairs, polynucleotides having complementary base pairs, and the like.

"Primer" is a polynucleotide capable of selectively annealing to a specified target sequence and thereafter serve as a point of initiation of a primer extension reaction wherein the primer is extended in the 3'→5' a 5'→3' direction, typically the latter.

II. Materials Used in the Method of the Invention

A. Target Nucleic Acid

The target nucleic acids for use with the invention may be derived from any living or once living organisms, including but not limited to prokaryotes, eukaryotes, plants, animals, and viruses, as well as synthetic nucleic acids. The target nucleic acids may originate from any of a wide variety of sample types, such as cell nuclei (e.g., genomic DNA) and extranuclear nucleic acids, e.g., plasmids, mitrochondrial nucleic acids, and the like. The target nucleic acids can include DNA or RNA, and are usually DNA.

Many methods are available for the isolation and purification of a target nucleic acid for use in the present invention. The preferred purification method should provide target nucleic acid sufficiently free of protein to allow efficient primer extension and nucleic acid amplification. Preferred purification methods include (i) organic extraction followed by ethanol precipitation, e.g., using a phenol/chloroform organic reagent (Ausubel), preferably using an automated DNA extractor, e.g., the Model 341 DNA Extractor available from PE Applied Biosystems (Foster City, Calif.); (ii) solid phase adsorption methods (Walsh, Boom); and (iii) salt-induced DNA precipitation methods (Miller), such methods being typically referred to as "salting-out" methods. Optimally, each of the above purification methods is preceded by an enzyme digestion step to help eliminate protein from the sample, e.g., digestion with proteinase K, or other like proteases.

To increase sensitivity, preferably the target nucleic acid is amplified prior to performing the method using a suitable nucleic acid amplification procedure. Such amplification may be linear or exponential. In a preferred embodiment, amplification of the target nucleic acid is accomplished using the polymerase chain reaction (PCR) (Mullis). Generally, the PCR consists of an initial denaturation step which separates the strands of a double stranded nucleic acid sample, followed by the repetition of (i) an annealing step which allows amplification primers to anneal specifically to positions flanking a target sequence; (ii) an extension step which extends the primers in a 5'→3' direction thereby forming an amplicon nucleic acid complementary to the target sequence, and (iii) a denaturation step which causes the separation of the amplicon and the target sequence. Each of the above steps may be conducted at a different temperature, where the temperature changes may be accomplished using a thermocycler (PE Applied Biosystems, Foster City, Calif.).

The generalized structure of a target nucleic acid for use in the present invention is shown in FIG. 1 where the target nucleic acid 5 includes a 5'-flanking portion 10 including a primer complementary portion 15, a 3'-flanking portion 25, and a repeat region 20 located between the 5'-flanking portion and the and the 3'-flanking portion. The repeat region 20 of the target nucleic acid comprises multiple repeat units $(R)_n$ 21 where R indicates a repeat unit and n designates the number of repeat units making up the repeat region. The repeat unit R may be any type of repeat motif, for example, but not limited to a microsatellite repeat (Webber and May; Smeets; Williamson), a minisatellite repeat (Jeffreys, Caskey), or an α-satellite repeat (Jabs).

The repeat region may be made up of multiple types of repeat units or repeat units which are themselves polymorphic.

B. Primer

Primers for use in the present invention are designed to obtain a balance between specificity of primer annealing, i.e., the frequency with which an undesired target sequence participates in a primer extension reaction, and efficiency of primer extension, i.e., the extent to which a desired target sequence participates in the primer extension reaction.

Specificity of primer annealing is generally controlled by the length of the primer and the temperature of the annealing reaction. Polynucleotides between about 18 and 24 bases are preferred because such polynucleotides tend to be very sequence specific when the annealing temperature is set within a few degrees of a primer melting temperature (Dieffenbach). To facilitate primer extension, a 3'-end of the primer includes an —OH group or other moiety which allows incorporation of a nucleotide onto the 3'-end of the primer. There exist a number of computer programs to facilitate primer selection in different contexts (Osborne; Montpetit).

In a preferred embodiment, the sequence of the primer is selected such that the primer anneals to the primer complementary portion of the 5'-flanking portion of the target nucleic acid. Preferably, the primer anneals such that a 3'-end of the primer is adjacent to a 5'-end of a repeat region of a target nucleic acid. However, the primer may also anneal to a segment of the repeat region of the target nucleic acid so long as it is at least partially anchored to the 5'-flanking portion of the target.

For embodiments of the invention which employ sample identifier tags and arrays of tag complements, the invention utilizes a plurality of extendable, different-sequence primers for detecting target sequences of interests. In one embodiment, the tagged primer includes a target binding segment, a tag segment, and an extendable primer end (5' or 3'). The target binding segment includes a polynucleotide sequence which is selected to bind to a selected target sequence. The tag segment contains a unique polynucleotide sequence that allows identification of the target binding segment to which the tag segment is attached. The tag segment can be directly attached to the distal end of the target binding segment, or is optionally linked to the tag segment by an intervening spacer group. In another embodiment, the tag segment is linked to an internal site within the target binding segment. Thus, the tag can be linked to an intersubunit linking group, or to a nucleotide base, within the target binding segment. Preferably, the tag is attached to an end of the target binding segment that is distal with respect to the extendable end of the primer.

The sequence of each target binding segment is selected to hybridize to a selected complementary target which contains a potential polymorphism or mutation, preferably such that the 3'-end of the primer is adjacent to a 5'-end of a repeat region of a target nucleic acid (for extension in the 5' to 3' direction). However, the primer may also anneal to a segment of the repeat region of the target nucleic acid so long as it is at least partially anchored to the 5'-flanking portion of the target.

The length of the target binding segment in each tagged primer is selected to ensure specific hybridization of the primer to the desired target, without significant cross-hybridization to non-target nucleic acids in the sample. Also, to enhance primer specificity, it is preferred that the melting temperatures of the target binding segments are within a few degrees of each other. Preferably, the melting temperatures of the target binding segments fall within a $\Delta$Tm range (Tmax–Tmin) of 10° C. or less, and preferably 5° C. or less. This can be accomplished by suitable choice of binding segment lengths based on known methods for predicting primer melting temperatures (Breslauer, 1986; Rychlik, 1989 and 1990; Wetmur, 1991; Osborne, 1991; Montpetit, 1992) for example. As above, target binding segments between about 18 and 24 bases in length are preferred.

The tag segment in each tagged primer is designed to contain a sequence that uniquely identifies the attached target binding segnment. Thus, the tag sequences should be selected to rinimiie (1) internal, self-hybridization, (2) hybridization with other same-sequence tags, (3) hybridization with other, different sequence tag complements, (4) and hybridization with the sample polynucleotides. Also, it is preferred that each tag can specifically recognize and hybridize to its corresponding tag complement under the same conditions for all tags in the primers.

Tag sequences can be selected by any suitable method. For example, computer algorithms for selected non-crosshybridizing sets of tags are described in Brenner (1996) and Shoemaker (1997). Preferably, the tag sequences have strands that are within a preselected temperature range, as discussed above with respect to the extendable primers. Preferably, the melting temperatures of the target binding segments fall within a $\Delta$Tm range (Tmax–Tmin) of 10° C. or less, and preferably within 5° C. or less, as calculated using any of the methods above (e.g., Breslauer). Preferably, the tag segments are at least 12 bases in length to facilitate specific hybridization to corresponding tag complements. Typically, tag segments are from 12 to 60 bases in length, and typically from 15 to 30 bases in length.

Tags and tag complements may be single or double stranded, such that sequence specific hybridization forms either duplexes by Watson and Crick base-pairing, or triplexes by forward or reverse Hoogsteen bonding. In embodiments where specific hybridization occurs via triplex formation, codina of tag sequences follows the same principles as for duplex-forming tags; however, there are further constraints on the selection of word sequences. Generally, third strand association via Hoogsteen type of binding is most stable along homopyrimidine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands.

There is extensive guidance in the literature for selecting appropriate sequences, orientation, conditions, nucleoside type (e.g. whether ribose or deoxyribose nucleosides are employed), base modifications (e.g. methylated cytosine, and the like in order to maximize, or otherwise regulate, triplex stability as desired in particular embodiments, e.g., Brenner (supra). More generally, conditions for annealing single-stranded or duplex tags to single-stranded or duplex sequence complements are well known, e.g. Brenner (supra), Ji et al. (1993), Cantor et al. (supra), Wetmur (1991), Breslauer et al. (1986), Schena (1995), and the like.

Preferably, polynucleotides such as primers are synthesized conventionally on an automated DNA synthesizer, e.g., PE Applied Biosystems (Foster City, Calif.) model 392 or 394 DNA/RNA Synthesizer, using standard chemistries, e.g., phosphoramidite chemistry (Beaucage). In an alternative method, primers can be isolated from a biological source.

C. Solid Phase Supports

In a preferred embodiment of the method of the invention, a target-primer hybrid is attached to a solid phase support during a separating step. Such attachment may be through either the target nucleic acid or the primer polynucleotide.

Solid phase supports for use with the invention may have a wide variety of forms, including microparticles, beads, membranes, slides, plates, micromachined chips, and the like. In addition, solid phase supports of the invention may comprise a wide variety of compositions, including glass, plastic, silicon, alkanethiolate-derivatized gold, GaAs, copper, germanium, cellulose, low cross-linked and high cross-linked polystyrene, crosslinked polyacrylamide matrices, silica gel, polyamide, membranes such as nylon, polyvinylidine difluoride (PVDF), or poly-tetrafluoroethylene, and the like.

Where attachment of the target-primer hybrid is through the primer, primers may be used with a solid phase support on which they were synthesized, or they may be separately synthesized and attached to a solid phase support for use during or before the separation step of the method.

When primers are synthesized on and used with the same solid phase support, such support may comprise a variety of forms and include a variety of linking moieties. Such supports may comprise microparticles or planar arrays, or matrices of regions having substantially uniform populations of primers. A wide variety of microparticle synthesis supports may be used with the invention, including microparticles made of controlled pore glass (CPG), highly cross-linked polystyrene, acrylic copolymers, cellulose, nylon, dextran, latex, polyacrolein, and the like. Microparticle supports frter include commercially available nucleoside-derivatized CPG and polystyrene beads (e.g. available from Applied Biosystems, Foster City, Calif.); derivatized magnetic beads; polystyrene grafted with polyethylene glycol (e.g., TentaGel, Rapp Polymere, Tubingen Germany); and the like. Selection of the support characteristics, such as material, porosity, size, shape, and the like, and the type of linking moiety employed depends on the conditions under which the primers are used. For example, in the present invention, supports and linkers that minimize steric hindrance of the polymerase enzymes and that facilitate access to nucleotide substrate are preferred. Other important factors to be considered in selecting the most appropriate microparticle support include size uniformity, efficiency as a synthesis support, degree to which surface area known, and optical properties, e.g., clear smooth beads provide instrumentational advantages when handling large numbers of beads on a surface.

As mentioned above, primers may also be synthesized on a single (or a few) solid phase supports to form an array of regions uniformly coated with primers. That is, within each region in such an array the same primer is synthesized. Techniques for synthesizing such arrays are disclosed elsewhere (Pease; Southern).

When primers are separately synthesized, and subsequently attached to a solid phase support for use, the primer may be attached to the support through a covalent linkage or a non-covalent linkage. When the primer is attached to the solid support through a non-covalent linkage, the primer includes one member of specific binding pair, e.g., biotin, the other member of the pair being attached to the solid support, e.g., avidin. Several methods are available for covalently linking polynucleotides to solid supports, e.g., through reaction of a 5'-amino polynucleotide with an isothiocyanate-functionalized glass support (Guo). A wide range of exemplary linking moieties for attaching primers onto solid supports either covalently or non-covalently are disclosed elsewhere. (Pon; Webb; Barany; Damha; Beattie; Maskos and Southern).

Where attachment of the primer-template hybrid is through the template nucleic acid, and he template nucleic acid is a PCR amplicon, the means for covalent or non-covalent attachment may be incorporated into a PCR primer used to effect the PCR. Thus, the PCR primer may contain a member of a specific binding pair, e.g., biotin, or a reactive moiety which can react with a functionalized solid support to form a covalent linkage, e.g., a 5'-amino group which reacts with a an isothiocyanate-functionalized glass support.

As noted above, the invention also utilizes a set of tag complements which are complementary to corresponding tag sequences in the tagged primers. The tag complements are provided as an addressable array, according to the design choice of the user. By "addressable array" is meant that the sequence of the target binding segment of each primer is known or can be determined from the position of hybridization of each primer on the array. Preferably, the tag complements are immobilized in discrete regions on a planar surface, such that each discrete region contains only tag complements having a particular sequence, and such that the sequence of the tag complement at each different discrete region is known. Conveniently, the tag complements are distributed as a periodic two-dimensional array of discrete tag complement regions which can be indexed via X and Y coordinates, or any equivalent thereof. Tag complements can be attached to appropriate solid phase support materials following the same considerations as for attachment of primers, discussed above.

To reduce the amounts of assay reagents used for tag detection, and to facilitate the sequencing of large numbers of fragment sequences, the arrays are preferably formed as microarrays having tag complement region densities of greater than 100 regions/cm$^2$, 300 regions/cm$^2$, 10$^3$ regions/cm$^2$, 3×10$^3$ regions/cm$^2$, 10$^4$ regions/cm$^2$, 10$^5$ regions/cm$^2$, or 10$^6$ regions/cm$^2$. In addition, the number of different sequence tag complements in each array is preferably equal to or greater than 10, 20, 50, 100, 200, 500, 1000, 3000, 10,000, 30,000, 100,000, or 300,000.

D. Labeled Nucleotides

In the methods of the present invention, one or more extendible nucleotides and/or nucleotide terminators include a label. The label is attached to the nucleotide in such a way that the label does not substantially interfere with polymerase-mediated incorporation of the labeled nucleotide in a primer extension reaction. Many alternative methods are available for labeling nucleotides in a mainer suitable for use with the present invention (Kricka). In a preferred class of labeling methods, a nucleoside base of the nucleotide is modified to include a label, i.e., the N-6 position of a purine base or the C-5 position of a pyrimidine base. A particularly preferred class of labeled nucleotides are the propargylethoxyamino nucleotides (Khan).

In one preferred embodiment of the invention, a labeled extendible nucleotide is capable of being rendered undetectable, e.g., upon treatment with a suitable reagent or electromagnetic radiation. In this embodiment, the labeled extendible nucleotide may be rendered undetectable by either removing the label from the nucleotide or by destroying the signal-producing properties of the label.

Several methods are available for attaching a label to an extendible nucleotide such that the label may be easily removed. Exemplary cleavable linkers for linking a label to a nucleotide include but are not limited to (N-[4-(p-azidosalicylamido)butyl]-3'-[2'-pyridyldithio]propionamide (APDP), (bis[2-(succinimidooxycarbonyloxyl)ethyl]sulfone (BSOCOES), disuccininimdyl tartarate (DST), and ethylene glycobis-[succinimidylsuccinate] (EGS), and the like (Pierce Catalog).

Preferred labels whose signal producing properties may be destroyed upon treatment with a suitable reagent or electromagnetic radiation include fluorescent labels whose fluorescent properties may be destroyed by photodestruction through exposure to high intensity light or by chemical degradation through treatment with oxidizing chemicals, e.g., oxygen, sodium hypochlorite, permanginate and the like. Alternative preferred classes of labels include enzymes, which may be rendered undetectable by reaction with an irreversable enzyme inhibitor or by denaturation, and chemiluminescent labels which can undergo only a single light-producing transformation and are thus autodestructing.

E. First and Second Primer-Extension Reagents

The present invention includes first and second primer extension reagents that, when used according to methods of the invention, enable the extension of a primer to proceed in discrete increments of single repeat units, i.e., the primer is extended only by one repeat unit per discrete primer extension reaction cycle.

The first primer extension reagent of the invention includes a set of extendible nucleotides which allow a primer extension reaction to proceed only to the extent that a primer is extended by an amount less than a full repeat unit. Thus, depending on the particular sequence of the repeat unit, the first primer extension reagent may include a variety of possible extendible nucleotide combinations. For example, if the sequence of the repeat unit is AGCT, the first primer extension reagent could include extendible nucleotides T (complementary to A), T and C (complementary to A and G), or T and C and G (complementary to A and G and C). However, to prevent uncontrolled continuous primer extension, the first primer extension reagent may not contain all extendible nucleotides T and C and G and A.

In certain situations, it is desirable to sub-divide the first primer extension reagent into separate sub-reagents such that each sub-reagent includes extendible nucleotides sufficient to allow extension of a primer only to the extent that a sub-portion of the repeat sequence is formed. For example, if the repeat unit is ATGCCGT, one sub reagent of the first primer extension reagent could include extendible nucleotides T, A, and C, while another sub-reagent of the first primer extension reagent could include extendible nucleotides G, and C.

The second primer extension reagent of the invention includes a set of extendible nucleotides which allow a primer extension reaction to proceed only to the extent that the portion of a repeat unit not synthesized by the first primer extension reagent is synthesized. Thus, depending on the particular sequence of the repeat unit and the composition of the first primer reagent, the second primer extension reagent may include a variety of possible nucleotide combinations. Continuing the example discussed above, if the sequence of the repeat unit is AGCT and the first primer extension reagent includes extendible nucleotides T and C, the second primer extension reagent may include extendible nucleotides G and A.

F. Primer Termination Reagent

The present invention includes a primer termination reagent for causing the termination of primer extension such that once a primer extension product has reacted with the primer termination reagent, no further primer extension may be accomplished.

The primer termination reagent of the invention includes one or more nucleotide terminators, and optionally, a set of extendible nucleotides which allow a primer extension reaction to proceed only to the extent that a primer is extended by an amount less than a full repeat unit in a primer extension reaction. Thus, depending on the particular sequence of the repeat unit, the sequence of the 3'-flanking portion of the target nucleic acid, and the composition of the first and second primer extension reagents, the primer termination reagent may include a variety of possible extendible nucleotide and nucleotide terminator combinations. For example, if the sequence of the repeat unit is AGCT, and the first nucleotide of the 3'-flanking portion is G, and the first and second primer extension reagents include the extendible niucleotides T, C, G and A, the primer termination reagent would include only the nucleotide terminator C, such nucleotide terminator being complementary to the G located in the 3'-flanking portion. Alternatively, if the first and second primer extension reagents only include the extendible nucleotides T and C, the primer termination reagent would include extendible nucleotides G and A and nucleotide terminator C.

In certain aspects of the present invention, the primer termination reagent includes a labeled nucleotide terminator. The labeling of the nucleotide terminator is accomplished essentially as described above in Section D.

III. The Method

Figure 2A:
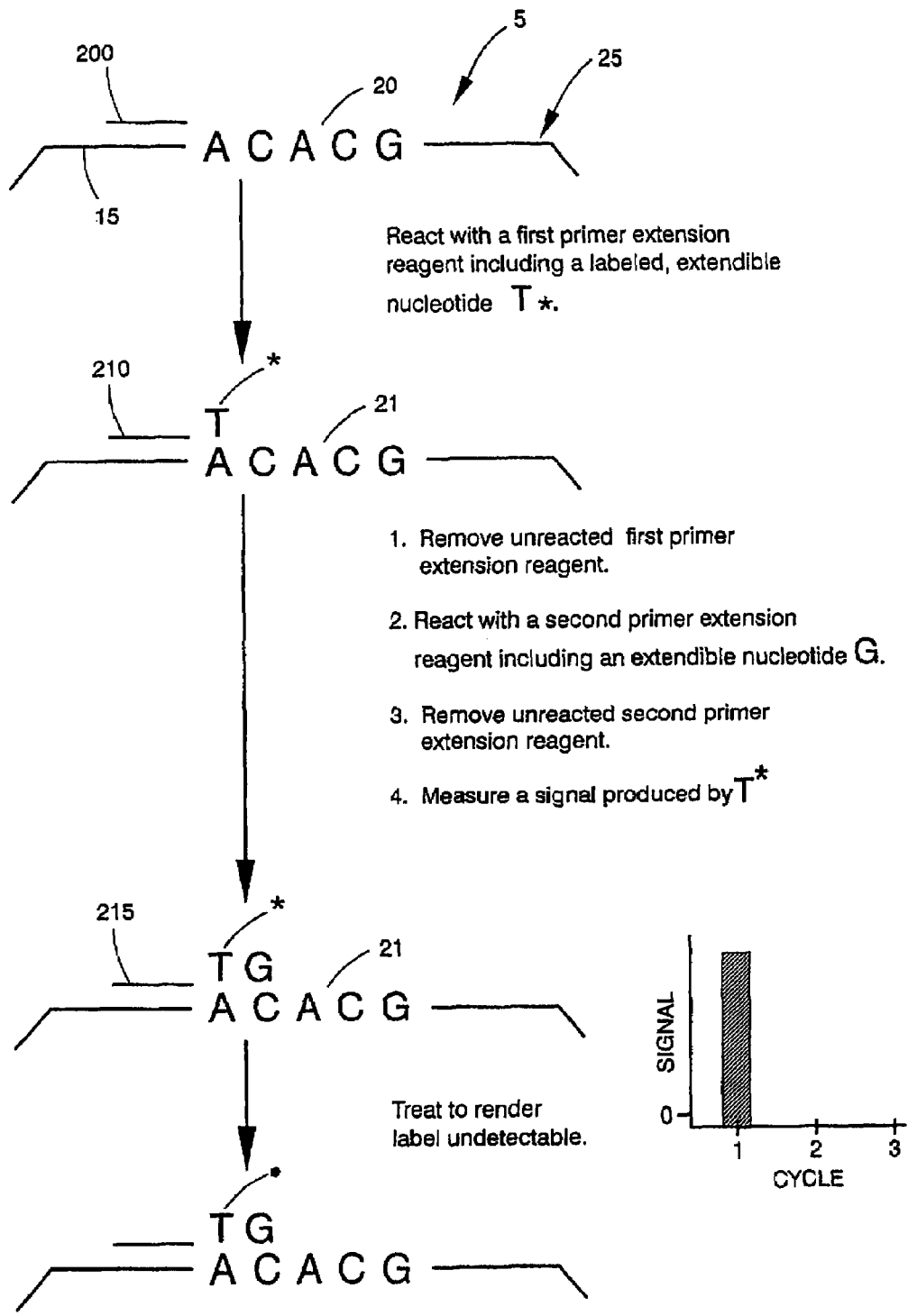
FIGS. 2A-C show a first aspect of the method of the invention wherein an extendible nucleotide is labeled and the label is rendered undetectable subsequent to each discrete increment of primer extension.
Figure 2B:
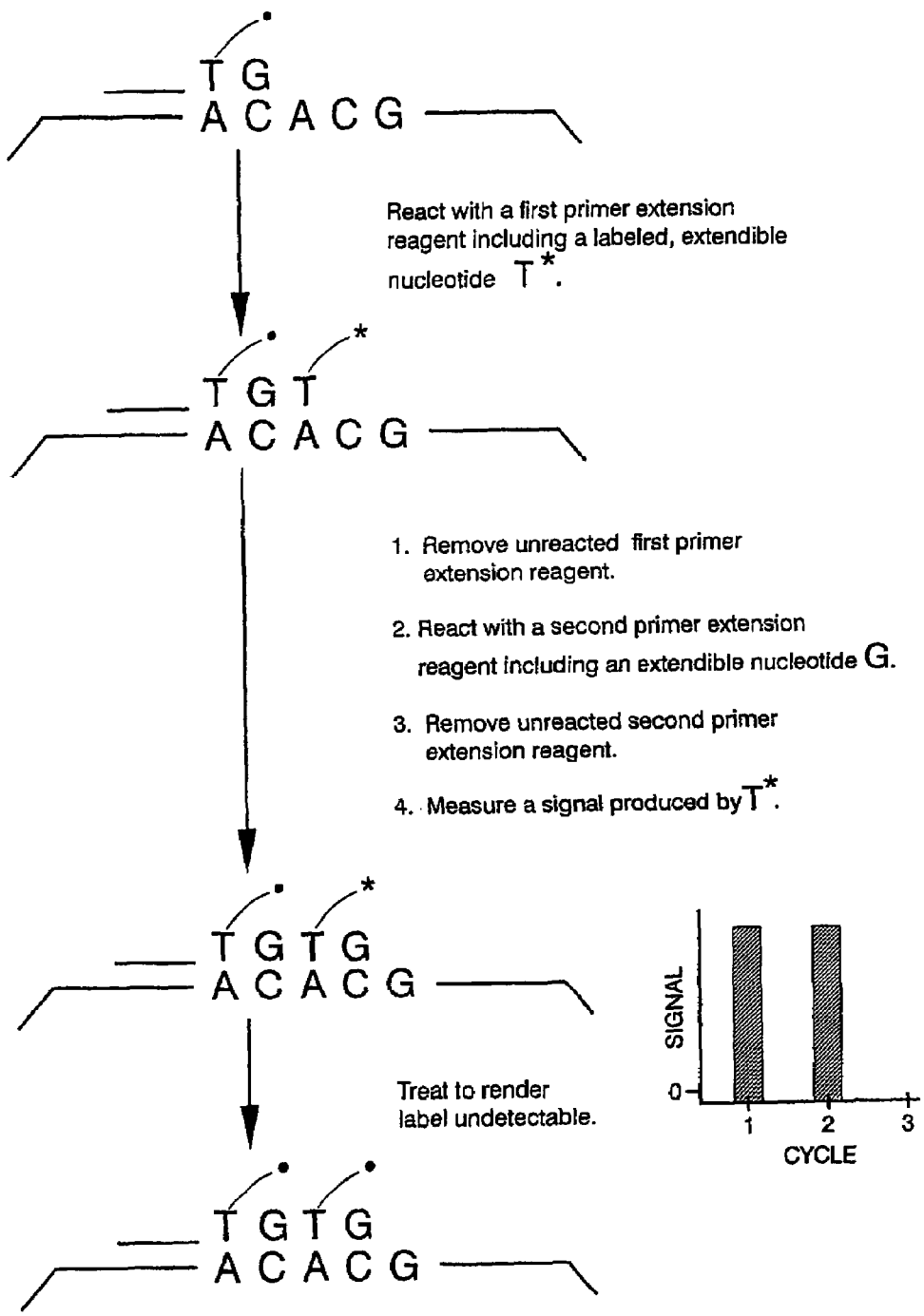
Figure 2C:
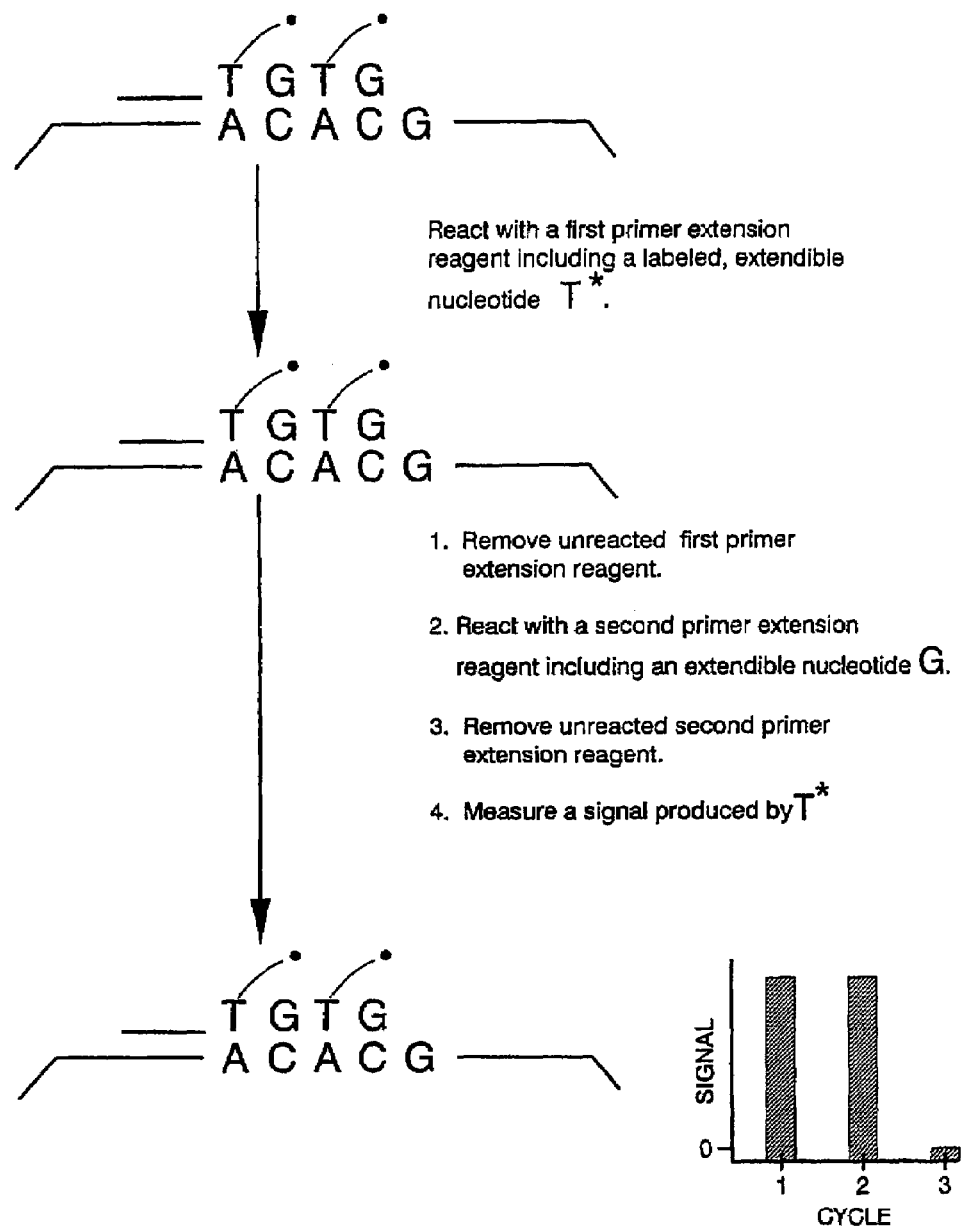

A preferred embodiment of a first aspect of the method of the invention is schematically depicted in FIGS. 2A-C. In the figure, the method is applied to a target nucleic acid 5 having a repeat region 20 made up of two copies of a two-base repeat having the sequence "AC" and a 3'-flanking portion 25 having a G nucleotide abutting the repeat region. In this preferred embodiment of the first aspect, a primer 200 is annealed to a primer-complementary portion 15 of the target nucleic acid 5 thereby forming a target-primer hybrid. The target-primer hybrid is then reacted with a first primer-extension reagent including a labeled extendible nucleotide T, resulting in the incorporation of the labeled T nucleotide into the 3'-end of a primer extension product 210. Following reaction with the first primer extension reagent, the first primer extension reagent is separated from the target-primer hybrid and the target-primer hybrid is reacted with a second primer-extension reagent including an extendible G nucleotide, resulting in the addition of the G nucleotide into a 3'-end of the primer extension product 215. Next the unreacted second primer extension reagent is separated from the target-primer hybrid and a measurement is performed to determine the amount of labeled extendible nucleotide incorporated into the primer extension product. As indicated by the histogram in the figure, at this point in the process, a large signal is detected, indicating the presence of the incorporated labeled T nucleotide. Finally, in order to prepare the target-primer hybrid for a subsequent discrete primer extension reaction cycle, the label attached to the incorporated extendible nucleotide is rendered undetectable. In the example the above described process steps are repeated two more times as shown in FIGS. 2B and 2C. In the third cycle shown in FIG. 2C, the intensity of the measured signal is substantially reduced as compared to the signal intensities seen in the first two cycles because the labeled extendible nucleotide T can not be incorporated into the primer extension product at this point. Thus, this reduction in the measured signal seen in the third cycle indicates that the repeat region only contains two copies of the AC repeat unit.

Figure 3A:
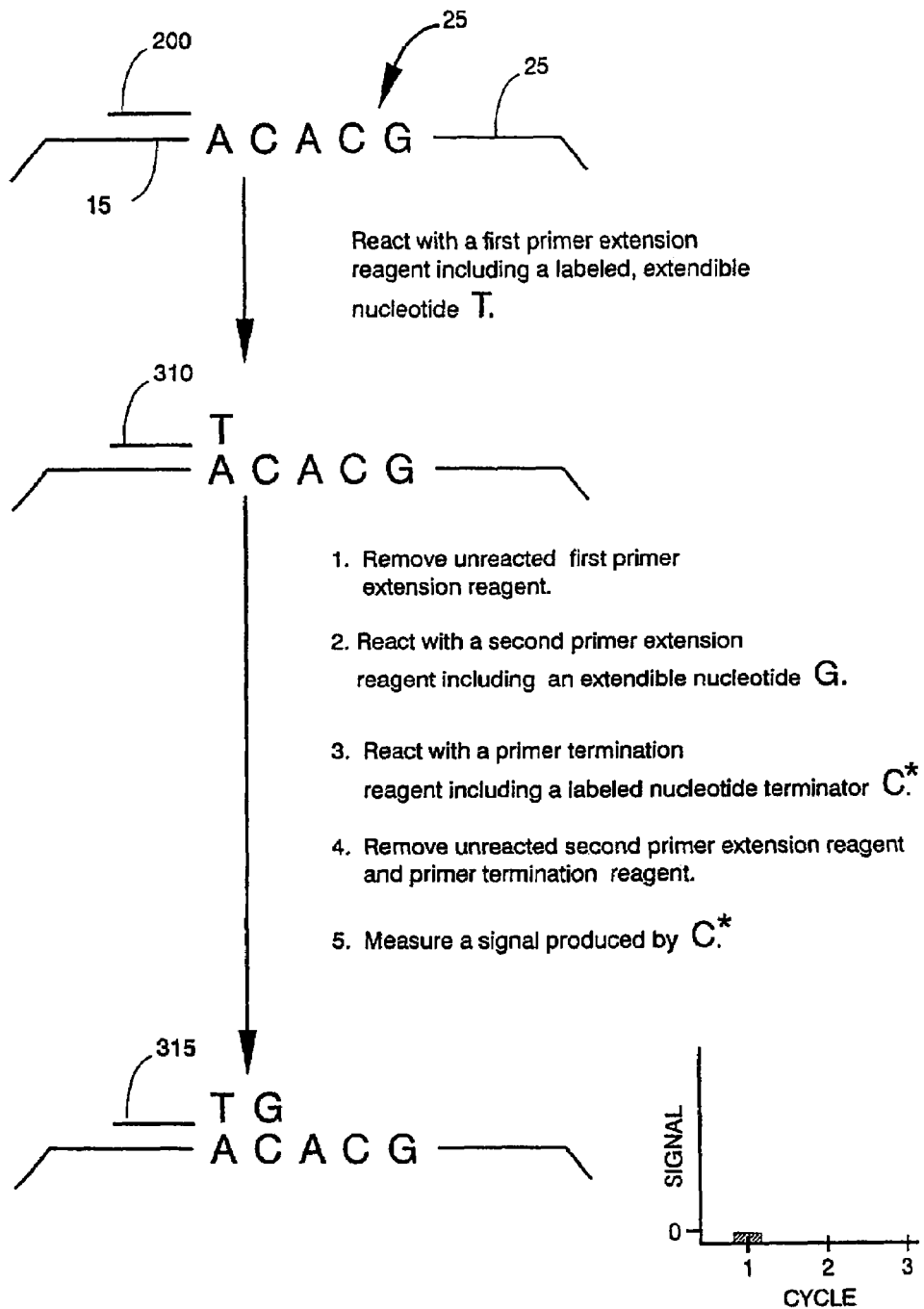
FIGS. 3A-B show a second aspect of the method of the invention wherein a nucleotide terminator is labeled.
Figure 3B:
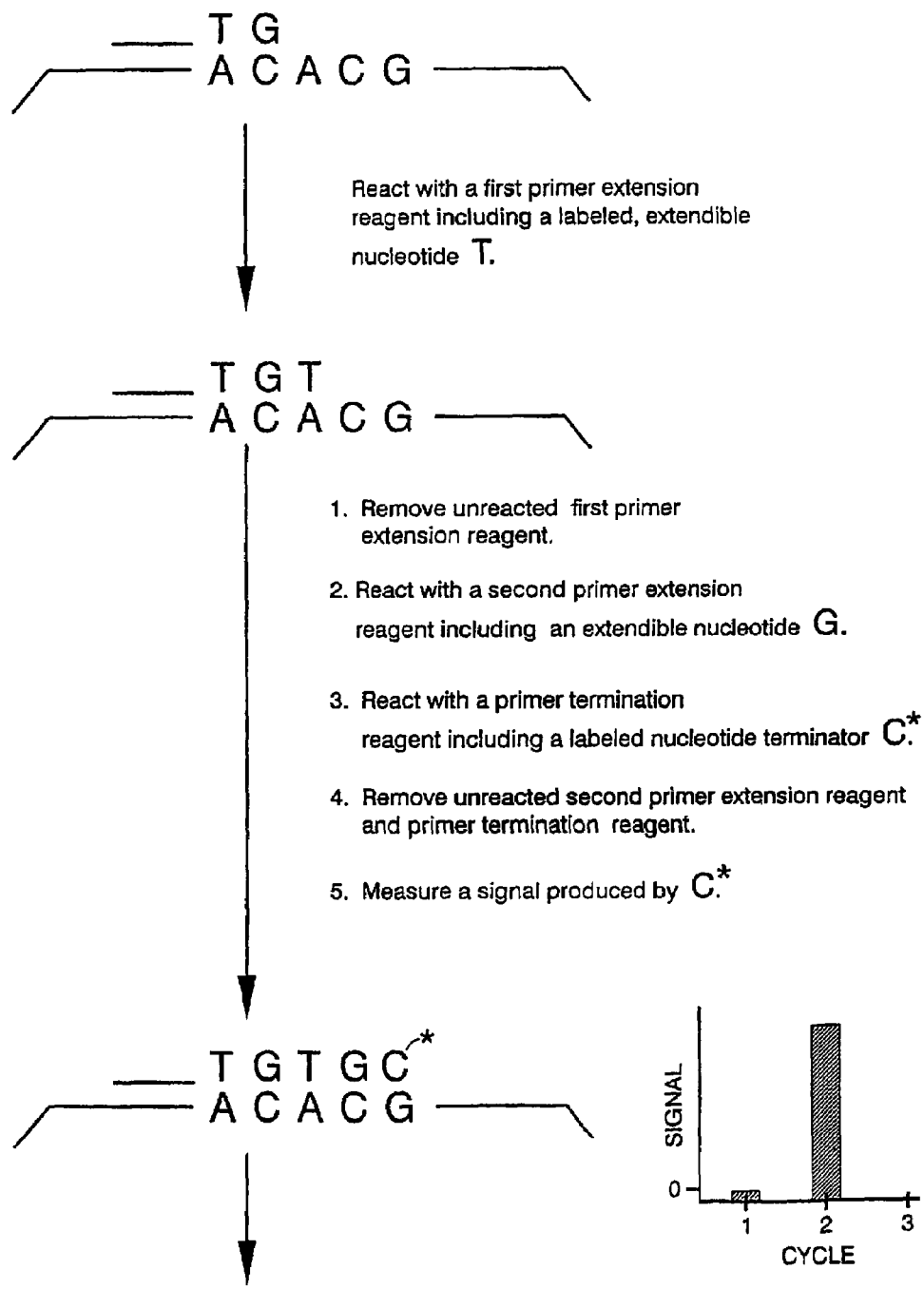

A preferred embodiment of a second aspect of the method of the invention is shown in FIGS. 3A-B. As before, the method is applied to a target nucleic acid having a repeat region made up of two copies of a two-base repeat having the sequence "AC" and a 3'-flanking portion having a G nucleotide abutting the repeat region. In this preferred embodiment of the second aspect, as before, a primer 200 is annealed to a primer-complementary portion 15 of a target nucleic acid 5 thereby forming a target-primer hybrid. The target-primer hybrid is then reacted with a first primer-extension reagent including an unlabeled extendible nucleotide T, resulting in the incorporation of the unlabeled T nucleotide into the 3'-end of a primer extension product 310. Following reaction with the first primer extension reagent, the first primer extension reagent is separated from the target-primer hybrid and the target-primer hybrid is reacted with a second primer-extension reagent, including an extendible G nucleotide, and a primer termination reagent including a labeled C nucleotide terminator, resulting in the addition of only the G extendible nucleotide into the 3'-end of the primer extension product 315. Next the unreacted second primer extension reagent and primer termination reagent are separated from the target-primer hybrid and a measurement is performed to determine the amount of labeled nucleotide terminator incorporated into the primer extension product. As indicated in the figure, at this point in the process, no signal is detected, indicating that the labeled nucleotide terminator is not incorporated into the primer extension product during this cycle of the process. In FIG. 3B, the above described process step is repeated. In this second cycle shown in FIG. 3B, the intensity of the measured signal is substantially increased as compared to the nominally zero signal intensity seen in the first step of the process because during the second step, the labeled nucleotide C terminator is incorporated into the primer extension product.

The following discussion provides a more detailed description of the above-described method steps of the first and second aspects of the invention.

A. Primer Annealing

The annealing reaction is performed under conditions which are stringent enough to guarantee sequence specificity yet sufficiently permissive to allow formation of stable hybrids at an acceptable rate. The temperature and length of time required for primer annealing depend upon several factors including the base composition, length and concentration of the primer, and the nature of the solvent used, e.g., the concentration of cosolvents such as DMSO, formamide, or glycerol, and counter ions such as magnesium. Typically, hybridization with synthetic polynucleotides is carried out at a temperature that is approximately 5 to 10° C. below the melting temperature of the target-primer hybrid in the annealing solvent. Preferably, the annealing temperature is in the range of 55 to 75° C. and the primer concentration is approximately 0.2 µM. Under these preferred conditions, the annealing reaction will be complete in only a few seconds.

B. Primer Extension Reaction

The time required to effect a primer extension reaction depends upon the length and concentration of the target sequence and upon the reaction temperature. Estimates for the rate of nucleotide addition under typical conditions vary from 35 to 100 nucleotides per second depending upon the buffer, pH, salt concentration, polymerase enzyme, and the nature of the DNA template.

In order to achieve a primer extension reaction which proceeds in discrete increments of single repeat units, according to the method of the invention, the primer extension reaction is divided into two independent steps: a first primer extension reaction and a second primer extension reaction. In the first primer extension reaction, the primer is extend by an amount less than the length of a single repeat unit, where control of the extent of primer extension is effected by the composition of a first primer extension reagent. In the second primer extension reaction, the primer is extended by an amount such that, in combination with the first primer extension reaction, the primer is extended by an amount equal to the length of a single repeat unit.

According to the first aspect of the method of the invention, one of the first or second primer extension reagents includes a labeled extendible nucleotide.

Also according to the first aspect of the method of the invention, in a variant of the above-described two-step discrete primer extension reaction, the second primer extension reagent includes a primer termination reagent. Thus, if after a second primer extension reaction the primer has been extended to the end of the repeat region of the target nucleic acid, a nucleotide terminator will be incorporated into the primer extension product thus prohibiting any further extension of that primer extension product. This is advantageous because it will remove the possibility that any spurious primer extension beyond the repeat region of the target nucleic acid will take place. This embodiment of the invention is particularly preferred where two alleles of a repeat sequence are being investigated simultaneously.

According to the second aspect of the invention, a primer termination reagent including a labeled nucleotide terminator is included in the second primer extension reaction. Preferably, the labeled nucleotide terminator is selected to be complementary to the nucleotide at the 3'-end of the 3'-flanking portion of the target nucleic acid which abuts the repeat region of such target nucleic acid.

C. Separation of Primer and Primer Extension Reagents

Between the first and second primer extension reactions, a separation step is performed to prevent the mixing of first and second primer extension reagents and thereby prevent uncontrolled primer extension. The means used to effect the separation step may be any means capable of separating the target-primer hybrid from the first and/or second primer extension reagents. Exemplary separation methods include but are not limited to HPLC, electrophoresis, liquid-liquid extraction, solid-liquid extraction, adsorption, and the like.

In a preferred embodiment, the target-primer hybrid is attached to a solid support during the separation step such that the primer extension reagents may be separated from the target-primer hybrid simply by washing the solid support.

According to this embodiment, the primer may be attached to the solid, support before or after performing the first primer extension reaction. The washing conditions are such that the target-primer hybrid is not substantially disrupted and non-specific adsorption of the primer extension reagents is minimized.

D. Measuring a Signal

Subsequent to either the first or second primer extension reaction, a detection step is performed wherein the amount of intact label which has been incorporated into a primer extension product is determined. Any detection method may be used which is suitable to the type of label employed. Thus, possible detection methods include radioactive detection, optical absorbance detection, e.g., UV-visible absorbance detection, optical emission detection, e.g., fluorescence or chemiluminescence.

The measuring step can take place at various points in the process depending upon the aspect of the invention being practiced and the composition of the first and second primer extension reagents. In the first aspect, preferably the measuring step takes place after the primer extension reagent including the labeled extendible nucleotide has been reacted with and separated from the target-primer hybrid. In the second aspect, the measuring step takes place after the primer termination reagent including the labeled nucleotide terminator has been reacted with and separated from the target-primer hybrid If the target-primer hybrid(s) are immobilized on a solid support for analysis, extended primers can be detected in an addressable array by scanning all or portions of each array simultaneously or serially, depending on the scanning method used. For fluorescence labeling, selected regions on an array may be serially scanned one-by-one or row-by-row using a fluorescence microscope apparatus, such as described in Fodor (1995) and Mathies et al. (1992). Hybridization patterns may also be scanned using a CCD camera (e.g., Model TE/CCD512SF, Princeton Instruments, Trenton, N.J.) with suitable optics (Ploem, 1993), such as described in Yershov et al. (1996), or may be imaged by TV monitoring (Khrapko, 1991). For radioactive signals (e.g., $^{32}P$), a phosphorimager device can be used (Johnston et al., 1990; Drmanac et al., 1992; 1993). Other commercial suppliers of imaging instruments include General Scanning Inc., (Watertown, Mass., www.genscan.com), Genix Technologies (Waterloo, Ontario, Canada; www.confocal.com), and Applied Precision Inc. Such detection methods are particularly useful to achieve simultaneous scanning of multiple tag complement regions.

E. Rendering A Label Undetectable

According to the first aspect of the method of the invention, once a signal from a label is detected, prior to performing a subsequent cycle of discrete primer extension, the label is rendered undetectable.

In one preferred embodiment, the label is rendered undetectable by cleaving the label off of the labeled extendible nucleotide incorporated in the primer extension product. The method used for cleaving the label from the nucleotide depends on the type of cleavable linkage used to link the label and the nucleotide. See above. Exemplary cleavage reagents include thiol, base, periodate, hydroxylamine and the like. In one preferred method, the label is attached to a base-portion of a uracil nucleotide and subsequent to detection the label is cleaved off of the labeled extendible nucleotide by treatment with the enzyme uracil N-glycosylase (UNG).

In a second preferred embodiment, the label is rendered undetectable by destroying the signal-producing properties of the label itself. Depending on the type of label used, there are several methods which may be employed for destroying the signal-producing properties of the label. For example, if the label is a fluorescent dye, the label may be rendered undetectable by photobleaching the dye using an intense light source in an oxygen-rich environment. If the label is an enzyme, the label may be rendered undetectable by reacting the label with an irreversible enzyme inhibitor which renders the enzyme incapable of catalyzing a signal producing reaction. If the label is a chemiluminescent agent which can undergo only a single light-producing transformation, the label is auto-distructing and thus does not require a separate reaction to render the label undetectable (Bronstein).

F. Tag Complement Arrays

As noted above, the invention also includes embodiments that utilize primers or sample polynucleotides that contain tag sequences that uniquely identify the attached primers or sample polynucleotides, which can be immobilized on addressable arrays for analysis of multiple sample polynucleotides in parallel.

A plurality of different-sequence primers are contacted with a polynucleotide sample under conditions effective for the primers to anneal to primer-complementary regions in one or more target polynucleotides, to form one or more target-primer hybrid(s), wherein either (1) each different-sequence primer contains (i) a target binding segment and (ii) a tag segment having a nucleotide sequence that uniquely identifies the target binding segment, or (2) one or more polynucleotides in the sample are tagged polynucleotides that contain a tag segment having a nucleotide sequence that uniquely identifies the attached polynucleotide. One or more primer extension cycles are performed as described above, and the appearance or loss of signal is determined at the appropriate times to measure repeat lengths.

Depending on the preferences of the user, the tagged primers or tagged sample polynucleotides can be contacted with an addressable array of immobilized, different-sequence tag complements which each contain a sequence that is complementary to one of the tag segments, under conditions effective to hybridize the tag segments to corresponding tag complements on the support. By way of illustration, embodiments using either tagged primers or tagged sample polynucleotides are shown in FIGS. 4 and 5, respectively, after the tag segments have been hybridized to a solid phase support, and a target-primer hybrid has been formed to yield tertiary polynucleotide complexes.

Figure 4:
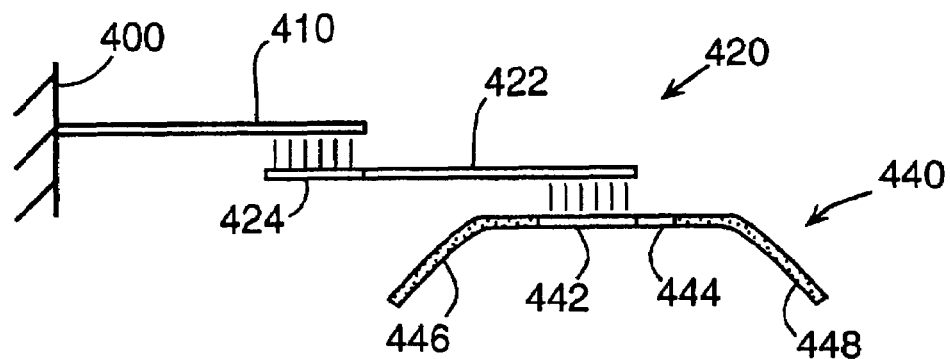
FIGS. 4 and 5 show exemplary schemes for practicing the invention using a solid phase support containing an array of tag complements for obtaining sequence repeat information for a plurality of different samples in parallel, using tagged primers or tagged sample polynucleotides.

FIG. 4 shows a tertiary complex wherein a tag complement oligonucleotide 410 immobilized on a solid phase support 400 is specifically hybridized to a tagged primer 420. Tagged primer 420 contains a target binding segment 422 and a tag segment 424. The vertical lines between the tag complement oligonucleotide 410 and tag segment 424 indicate complementary base-pairing. Also shown is a sample polynucleotide 440 comprising a sequence 442 which hybridizes to target binding segment 422, and which, in the embodiment shown, terminates at a nucleotide immediately adjacent to a sample repeat region 444. Sample polynucleotide 440 optionally includes flanking sequences 446 and 448 which do not hybridize to the tagged primer. Once polynucleotide 440 and tagged primer 420 have formed a target-primer hybrid, the hybrid can be treated as discussed in preceding sections to extend the extendable end of the primer into the repeat region of the sample polynucleotide. Extension cycles are repeated until the end of the repeat region has been reached, or the desired number of repeats have been counted.

Figure 5:
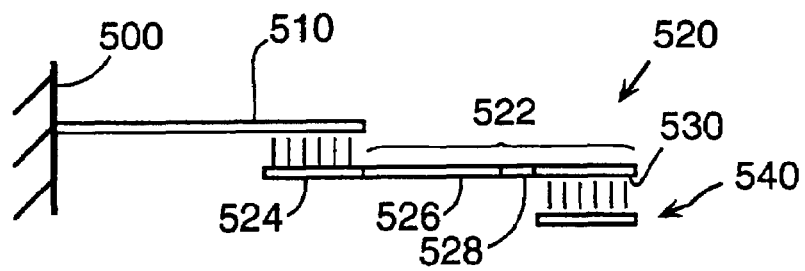

FIG. 5 shows an alternative tertiary complex wherein a tag complement oligonucleotide 510 immobilized on a solid phase support 500 is specifically hybridized to a tagged sample polynucleotide 520. Polynucleotide 520 includes a tag segment 524 which is hybridized to oligonucleotide 510, and which is connected to a sample sequence 522. Sequence 522 includes a repeat region 528 which is flanked on either side by first and second sample segments 526 and 530. An extendable primer 540 is annealed to one of sample segments 526 and 530 to form a target-primer hybrid such that the extendable end is adjacent to (or protrudes into) the sample repeat region 528. The hybrid can be treated as above to extend the extendable end of the primer into the repeat region of the sample polynucleotide, until the end of the repeat region has been reached.

Tagged sample polynucleotides can be formed by any suitable method. Conveniently, tagcged samples can be formed by PCR amplification using primer pairs comprising first and second target-specific primers which flank each sample sequence of interest, wherein one of the probes contains an identifier tag segment. In one embodiment, the tagged primer is constructed so that the tag segment is not copied during amplification, either due to the presence of non-standard internucleoside linkages (e.g., PNA linkages), or due to the presence of a non-polynucleotide linker region which separates the tag segment from the target-binding segment, as can be prepared by standard synthetic methods. After the tag segment is hybridized to a tag complement on an addressable array, the non-tagged strand can be removed from the tagged strand, e.g., by elevated temperature and/or reducing salt concentration to destabilize DNA-DNA duplex structure, particularly if either the tag melts from the tag complement at a higher temperature than the melting temperature between the target-binding segment of the primer and the sample polynucleotide. Many other approaches for obtaining a selected strand from duplex nucleic acids are known in the art, and include for example, (1) the use of a biotinylated primer in PCR to enable capture and separation of the non-tagged strand from the tagged strand under denaturing conditions, (2) the use of a PCR primer (non-tagged) that contains a short RNA segment which can be degraded with RNAse after PCR is complete, followed by destruction of the second RNAse degraded strand with an enzyme that has an exonuclease activity (e.g., an appropriate DNAse), or an asymmetric PCR method which favors amplification of the tagged primer strand.

Although FIGS. 4 and 5 show particular embodiments, it will be apparent that other variations can be used in accordance with the methods of the invention. For example, with reference to FIG. 5, extendable primer 540 can be designed to bind instead to sample segment 526, between the tag segment and the repeat region, such that the extendable end of the primer is again adjacent to sample repeat region 528.

The tagged primers or tagged sample polynucleotides can be hybridized to a tag complement array at any appropriate time during the primer extension process. For example, the tagged primers of sample polynucleotides can be immobilized on the support prior to the first contacting step in which the different-sequence primers and sample polynucleotides are annealed to form target-primer hybrids. Alternatively, immobilization can be performed after the first primer extension reaction, or after the second primer extension reaction. In the latter case, a small aliquot of the extension reaction mixture can be removed after each extension cycle and hybridized to replicate arrays, such that each replicate array provides counting information after each cycle.

IV. Kits for Practicing the Method

The present invention includes kits for carrying out the various aspects and embodiments of the methods of the invention. In a first aspect, kits of the invention include a primer, a first primer extension reagent, and a second primer extension reagent, wherein at least one of the first or second prinier extension reagents includes an extendible nucleotide having a label attached thereto. Preferably, the label attached to the extendible nucleotide may be rendered undetectable following a treatment step effective to cleave the label from a primer extension product and/or destroy the signal producing properties of the label. Preferably, the primer is bound to a solid support, or, is capable of being bound to a solid support through a specific binding pair or through a covalent linking moiety. In another preferred embodiment, this aspect of the invention includes a solid-phase support for attachment of a target-primer hybrid through the primer or the target nucleic acid. Optionally, the kits of this first aspect of the invention include a primer termination reagent.

In a second aspect, the kits of the invention include a primer, a first primer extension reagent, a second primer extension reagent, and a primer termination reagent, wherein the primer termination reagent includes a nucleotide terminator having a label attached thereto. The second primer extension reagent and the primer termination reagent may be packaged either separately or together as a mixture. Preferably, the primer is bound to a solid support, or, is capable of being bound to a solid support through a specific binding pair or through a covalent linking moiety. In another preferred embodiment, this aspect of the invention includes a solid-phase support for attachment of a target-primer hybrid through the primer or the target nucleic acid.

In another embodiment, the kits can include (A) a plurality of different-sequence primers, each containing (i) a target binding segment and (ii) a tag segment having a nucleotide sequence that uniquely identifies the target binding segment; a first primer extension reagent; and a second primer extension reagent, wherein at least one of the first or second primer extension reagents includes an extendible nucleotide having a label attached thereto; and/or (B) an addressable array of immobilized, different tag complements, wherein each different tag complement contains a sequence that is complementary to one of the primer tag segments, under conditions effective to hybridize the tag segments to corresponding tag complements on the support.

The invention may be further understood in light of the following examples, which are not intended to limit the invention.

EXAMPLE

The following study illustrates exemplary sample hybridization conditions and extension cycles for counting repeats in four different sample sequences using an array of target-specific capture oligonucleotides immobilized on a solid support.

A. Support Glass microscope slides were immersed in 1 N HNO$_3$ for 1 to 2 hours, followed by rinsing with deionized water. Optionally, slides were soaked overnight in 5% HCl to improve long-term stability of subsequent functionalizization. Slides were then sonicated sequentially in the following three solvents for 10 minutes each: hexane, acetone, and ethanol, followed by drying in air.

A solution of 2% (v/v) aminopropyltriethoxy silane (0.8 mL in 40 mL) in 95% acetone: 5% water was prepared in a disposable plastic Falcon tube. This amount of solution was usually sufficient to coat at least three slides. The solution was allowed to stand for 5 to 20 minutes to hydrolyze the ethoxy groups to hydroxyl groups. Air-dried slides were dipped in the solution for 2 minutes each, and then rinsed by dipping in three or more successive acetone baths.

The slides were cured in 100° C. oven for 45 minutes. Cured slides were treated for 2 hours with a 0.2% solution of 1,4-phenylene diisothiocyanate (PDITC) in 10% pyridine:dimethyl formamide, followed by washes in baths of methanol and acetone, and air-drying. The slides may be stored under vacuum with a dessicant at 4° C. Stacking the slides also helps preserve the functionalization and keeps the functinalized surfaces free from particulates. (In an alternative embodiment, instead of 1,4-phenylene diisothiocyanate, the cured slides can be treated with a 1 mM solution of EMCS (N-(ϵ-maleimido caproxyl) succinimide in methanol:dimethylsulfoxide (80:20) for 2 hours.)

B. Immobilization of Capture Oligos. Synthetic capture oligonucleotides were prepared by standard phosphoramidite synthetic methods. The capture oligonucleotides had the following general structure: 5'-amirno-[(PEO)$_2$]-[capture oligo (24 nt)], where PEO=—O— (CH$_2$CH$_2$O)$_6$ added via DMT-O—(CH$_2$CH$_2$O)$_6$-phosphoramidite. The capture oligonucleotides had polynucleotide sequences complementary to the double-underlined sequences in the four sample sequences shown in section C below.

The capture oligos were sported in a rectangular array pattern onto slides prepared as above using an ASYMTEC robotic loader (Asymtec, Carlsbad, Calif., Model No. C-708), with oligonucteotide concentrations of about 50 μM (in 100 mM Na$_2$CO$_3$, pH 9.0) and spotting volumes of about 0.2 to 1 nL. The pattern included a separate set of 8 spots (2×4 rows) for each different capture oligo to provide redundancy. The spots had diameters of about 200 micrometers and were spaced apart by 320 micrometers center-to-center. The robotic loader included a slide holder to hold the slides-during oligonucleotide deposition, and a blotting area for cleaning dispenser tips.

After spotting, the capture oligos were fixed onto the slides by incubating the slides in a humidity chamber at room temperature for 60 minutes, followed by soaking in 1% NH$_4$OH (aq) for 20 minutes and in 0.2% casein in TBS (50 mM Tris, 150 mM NaCl, pH 8) for 20 minutes. The slides were washed in deionized water and stored at 40° C.

C. Sample Hybridization and Analysis. Four different sample oligos were prepared to represent four different micrrosatellite alleles. In brief, the sample polynucleotides included the following sequences, where single-underlining indicates repeat regions, and double underlining indicates segments for hybridizing to complementary capture oligos on the support:

```
Sample Oligo 2260-2G (SEQ ID NO:1)
5'-GTCAGGACACAAAGTGATTTGATGTAGATTTTGA-3'

Sample Oligo 1411-1G (SEQ ID NO:2)
5'-GTCAGGACTGATAAAGTGTAAAAGTGTATGAT-3'

Sample Oligo 3149-2T (SEQ ID NO:3)
5'-GTCATTACACTGTATGATAAAGGATTTTGATTGA-3'

Sample Oligo 4223-4T (SEQ ID NO:4)
5'-GTCATTACACACACGTATTGATTTGATTGATTGAGATT-3'
```

A mixture of the four sample oligos (0.33 μM each in 1×PCR buffer containing 1.5 mM MgCl$_2$, 50 mmM KCl, 1:5 mM MgCl$_2$, 10 mM Tris-HCl, pH 8.3, and 0.001% (w/v) gelatin) was placed over the capture oligos on the array and allowed to incubate for 1 hour at room temperature. After the incubation, unbound oligos were removed with 1×TE (10 mM Tris, pH 8, 1 mM EDTA) contairnng 50 mM NaCl. Replicate slides were subjected to different numbers of extension cycles (one, two, three or four cycles). Each extension cycle (also called a "reagent cycle") involved the following steps:

1) Incubate slide for 4 minutes at 37° C. in an extension mixture containing:
   500 μM dGTP
   20 μM Big Dye R6G ddATP (Perkin-Elmer, Foster City, Calif., Emrax=560 nm)
   20 μM Big Dye dRox ddCTP (Perkin-Elmer, Foster City, Calif., Emax=615 nm)
   1 U/μL AMPLITAQ FS (plus 0.125 U/μL pyrophosphatase)
   1× buffer (80 mM Tris, pH 9.0, 2.5 mM MgCl$_2$)
2) Rinse slide with 1×TE containing 50 mM NaCl, then wash 3 times by immersion in same solution.
3) Incubate slide for 4 minutes at 37° C. in an extension mixture containing:
   500 μM dATP
   20 μM Big Dye R6G ddATP (Perkin-Elmer, Foster City, Calif., Emax=560 nm)
   20 μM Big Dye dRox ddCTP (Perkin-Elmer, Foster City, Calif., Emax=615 nm)
   1 U/μL AMPLITAQ FS (plus 0.125 U/μL pyrophosphatase)
   1× buffer (80 mM Tris, pH 9.0, 2.5 mM MgCl$_2$)
4) Rinse slide with 1×TE containing 50 mM NaCl, then wash 3 times by immersion in same solution.

After 4 extension cycles had been completed (each cycle included steps 1 through 4), each slide was overlayed with a viewing buffer containing 50% (w:v) urea and 1×TBE (0.09 M Tris-borate, 2 mM EDTA, pH ~8.3) to provide an alkaline pH environment to enhance the fluorescence emissions of the dye labels.

The slides were each viewed using an imaging device set for fluorescence emission detection at 560 nn and 610 nm. The device was an imaging fluorimeter that produces a two-dimensional image array of emission intensities (electronic image). Each point in the image array corresponds to a physical location on the sample slide. The excitation source is a 40 mW argon ion laser. The excitation wavelength can be selected from either of two natural laser lines (488 nm and/or 514 nm). The selection of laser wavelengths is accomplished by passing the beam which contains light of both wavelengths through one of three filters. The selected filter will pass either 488 nm only, 514 nm only, or both 488 and 514 nm. The filters are mounted on a moter driven platform so that the selection can be performed under computer control. The beam containing either or both wavelengths passes through a classical beam expander. The collimated expanded beam is then directed into a commercially available assembly (Scanlab, Puchhein, Germany, Model SK1020) containing two orthogonal "galvo mirrors". This is a mechanical device designed to rotate each of the two mirrors quickly and precisely over a small angle. The axes of rotation are orthoganal and independent so that the beam can be rastered over a rectangular pattern, also under computer control.

The scanned beam is focused by an f-theta lens which forms a scanned laser spot at one focal length. The spot size is 20 µm diameter. Typically, it is stepped over an area of 20 mm×20 mm in increments of 20 µm, thereby forming a 1000× 1000 array of pixels. The focused laser spot is formed after passing through a dichroic beam splitter which is designed to reflected the laser excitation wavelengths but transmit the fluorophore emission.

As the laser beam steps across a fluorescent region, the fraction of fluorescence radiation within the solid angle of collection of the emission optics is transmitted by the dichroic mirror and is collimated by a lens having a 150 mm focal length. The collimated beam is then filtered by a long pass interference filter which further rejects laser light. A second lens of 75 mm focal length focuses the beam onto the photocathode of a red sensitive photomultiplier tube (PMT). The PMT photocathode does not need to be carefully adjusted since the focus is not critical. A filter wheel in front of the PMT allows only a small wavelength band (10 nm) to reach the detector. The filter wheel can be adjusted to one of six positions to allow for emission of multiple fluorophores to be discriminated.

The electrical output of the PMT is proportional to the intensity of the light reaching the photocathode. The computer system is capable of storing the signals at each of an array of mirror positions to form the electronic image.

The results were as expected. Specifically, for oligo 1 (SEQ ID NO:1), no signal was observed until completion of the second cycle, after which two GT dimers and a fluorescence-labeled ddC terminator had been appended to the immobilized capture oligo, which also served as the extendable primer. Similarly, for oligos 2 through 4 (SEQ ID NO:2 through 4), the appropriate fluorescent signal was observed after 1, 2 and 4 extension cycles, respectively.

All publications and patent applications refered to in this disclosure are herein incorporated by reference to the same extent as if each individual publication or patent application was specifically and individually indicated to be incorporated by reference.

Although only a few embodiments have been described in detail above, those having ordinary skill in the molecular biology art will clearly understand that many modifications are possible in the preferred embodiments without departing from the teachings thereof. Accordingly, all such modifications are intended to be encompassed within the scope of the following claims.

We claim:

1. A kit useful for determining the number of repeat units in a repeat region of a target nucleic acid comprising: a plurality of different-sequence primers, each containing (i) a target binding segment and (ii) a tag segment having a nucleotide sequence that uniquely identifies the target binding segment, a first primer extension reagent; and a second primer extension reagent, wherein at least one of the first or second primer extension reagents includes an extendible nucleotide having a photodestructible label attached thereto.

2. The kit of claim 1, which further includes an addressable array of immobilized, different tag complements, wherein each different tag complement contains a sequence that is complementary to one of said primer tag segments, under conditions effective to hybridize the tag segments to corresponding tag complements on the support.

3. The kit of claim 1 wherein the label comprises a fluorescent molecule.

4. The kit of claim 1 wherein the label is attached to the extendible nucleotide through a cleavable linker.

5. The kit of claim 1, wherein the second primer extension reagent includes a nucleotide terminator having a label attached thereto.

6. The kit of claim 5, wherein the nucleotide terminator comprises a label selected from the group consisting of a fluorescent molecule and a chemiluminescent molecule.

7. The kit of claim 5, wherein the nucleotide terminator comprises a photodestructible label.

8. The kit of claim 1, further comprising a polymerase.

9. The kit of claim 8, wherein the polymerase is Taq DNA polymerase.

* * * * *